United States Patent
Arnoldy et al.

(10) Patent No.: US 6,777,579 B2
(45) Date of Patent: Aug. 17, 2004

(54) HYDROFORMYLATION PROCESS

(75) Inventors: Peter Arnoldy, Amsterdam (NL);
Robert Hardy Ellison, Chester (GB);
Herman Pieter Charles Eduard Kuipers, Amsterdam (NL); Robert Moene, Amsterdam (NL); Frederik Hendrik Van Der Steen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/294,320

(22) Filed: Nov. 14, 2002

(65) Prior Publication Data

US 2003/0176742 A1 Sep. 18, 2003

Related U.S. Application Data

(60) Provisional application No. 60/332,809, filed on Nov. 14, 2001.

(51) Int. Cl.[7] .............................................. C07C 45/50
(52) U.S. Cl. ........................ 568/429; 568/436; 568/454
(58) Field of Search ................................ 568/429, 436, 568/454

(56) References Cited

U.S. PATENT DOCUMENTS

| | | | |
|---|---|---|---|
| 3,369,050 A | 2/1968 | Greene | 260/632 |
| 3,420,898 A | 1/1969 | Van Winkle et al. | 260/632 |
| 3,440,291 A | 4/1969 | Van Winkle et al. | 260/632 |
| 3,448,157 A | 6/1969 | Slaugh et al. | 260/604 |
| 3,448,158 A | 6/1969 | Slaugh et al. | 260/604 |
| 3,501,515 A | 3/1970 | Van Winkle et al. | 260/439 |
| 3,976,703 A | 8/1976 | Wilkes | 260/632 |
| 4,151,209 A | 4/1979 | Paul et al. | 260/604 |
| 4,277,627 A | 7/1981 | Bryant et al. | 568/454 |
| 4,332,915 A | 6/1982 | Knifton et al. | 518/700 |
| 4,539,041 A | 9/1985 | Figlarz et al. | 75/0.5 A |
| 4,806,678 A | 2/1989 | Lin | 560/266 |
| 5,001,274 A * | 3/1991 | Bunning | 568/454 |
| 5,082,977 A * | 1/1992 | Chaung | 568/454 |

FOREIGN PATENT DOCUMENTS

EP 0024761 3/1981 ........... C07C/27/22

OTHER PUBLICATIONS

International Search Report of Mar. 6, 2003.
Shriver, D. F., *Organometallic surface chemistry: final report for period Jul. 1, 1983–Sep. 14, 1986,* Report No. DOE/ER/13104–2, Order No. DE87006812, Abstract Only, from Energy Res. Abstr. 1987, 12(12), Abstr. No. 25374.

* cited by examiner

*Primary Examiner*—Samuel Barts
*Assistant Examiner*—Sikarl A. Witherspoon

(57) ABSTRACT

A hydroformylation process is provided that involves reacting a compound having at least one olefinic carbon-to-carbon bond with hydrogen and carbon monoxide in the presence of a cobalt catalyst and a sulfur-containing additive which suppresses the formation of cobalt carbide in the reaction mixture.

70 Claims, No Drawings

HYDROFORMYLATION PROCESS

This application claims the benefit of U.S. Provisional Application No. 60/332,809 filed Nov. 14, 2001, the entire disclosure of which is hereby incorporated by reference

FIELD OF THE INVENTION

The present invention relates to a process for hydroformylating a compound having at least one olefinic carbon-to-carbon bond (also called an olefinic compound herein).

BACKGROUND OF THE INVENTION

Various processes for producing aldehyde and/or alcohol compounds by the reaction of a compound having at least one olefinic carbon-to-carbon bond with carbon monoxide and hydrogen in the presence of a catalyst are known. Typically, these reactions are performed at elevated temperatures and pressures. The aldehyde and alcohol compounds that are produced generally correspond to compounds obtained by the addition of a carbonyl or carbinol group, respectively, to an olefinically unsaturated carbon atom in the starting material with simultaneous saturation of the olefin bond. Isomerization of the olefin bond may take place to varying degrees under certain conditions with the consequent variation of the products obtained. These processes are typically known as hydroformylation reactions and involve reactions which may be shown in the general case by the following equation:

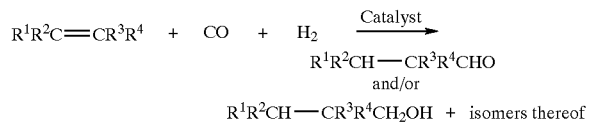

$$R^1R^2C=CR^3R^4 + CO + H_2 \xrightarrow{\text{Catalyst}}$$
$$R^1R^2CH-CR^3R^4CHO$$
and/or
$$R^1R^2CH-CR^3R^4CH_2OH + \text{isomers thereof}$$

In the above equation, each group $R^1$ to $R^4$ may independently represent an organic radical, for example a hydrocarbyl group, or a suitable atom such as a hydrogen or halogen atom, or a hydroxyl group. The above reaction may also be applied to a cycloaliphatic ring having an olefinic linkage, for example cyclohexene.

The catalyst employed in a hydroformylation reaction typically comprises a transition metal, such as cobalt, rhodium or ruthenium, in complex combination with carbon monoxide and ligand(s) such as an organophosphine.

Representative of the earlier hydroformylation methods which use transition metal catalysts having organophosphine ligands are U.S. Pat. Nos. 3,420,898, 3,501,515, 3,448,157, 3,440,291, 3,369,050 and 3,448,158.

In attempts to improve the efficiency of a hydroformylation process, attention has typically focussed on developing novel catalysts and novel processes for recovering and re-using the catalyst. In particular, novel catalysts have been developed which may exhibit improved stability at the required high reaction temperatures. Catalysts have also been developed which may permit the single-stage production of alcohols rather than a two-step procedure involving separate hydrogenation of the intermediate aldehyde. Moreover, homogeneous catalysts have been developed which may permit improved reaction rates whilst providing acceptable yields of the desired products.

The present invention seeks to solve problems associated with a hydroformylation process that employs a cobalt catalyst.

SUMMARY OF THE INVENTION

According to a first aspect, the present invention provides a hydroformylation process comprising reacting a compound having at least one olefinic carbon-to-carbon bond with hydrogen and carbon monoxide in the presence of a cobalt catalyst and a sulfur-containing additive which suppresses the formation of cobalt carbide during the reaction.

DETAILED DESCRIPTION OF THE INVENTION

We have detected that cobalt catalysts comprising cobalt in complex combination with carbon monoxide and a ligand may decompose during the reaction to produce cobalt carbide (a compound of cobalt and carbon, empirical formula $Co_xC$, where x is 2 or 3). Cobalt carbide is catalytically inactive in hydroformylation reactions, thereby resulting in an increased rate of catalyst usage. The cobalt carbide is not only catalytically inactive in hydroformylation reactions but also has a relatively bulky, porous structure and is insoluble in the reaction medium. This represents a significant disadvantage, particularly for homogeneous cobalt catalysts, because the cobalt carbide typically tends to agglomerate and form detrimental deposits on the internal surfaces of the production facility. The deposition of cobalt carbide impedes the running of a hydroformylation production facility with optimal efficiency.

The process according to the present invention addresses the aforementioned problems associated with hydroformylating a compound having an olefinic carbon-to-carbon bond in the presence of a cobalt catalyst. The inclusion of the sulfur-containing additive in the reaction mixture suppresses the formation of cobalt carbide compared with performing the corresponding hydroformylation reaction in the presence of the cobalt catalyst but without the additive. Thus, the formation of the cobalt carbide is suppressed during the hydroformylation reaction when the formation of cobalt carbide in the presence of the cobalt catalyst with the sulfur-containing additive is less than the formation of cobalt carbide in the presence of the cobalt catalyst without the sulfur-containing additive. Suitably, the additive reduces the formation of catalytically inactive cobalt carbide. The reduction in the formation of cobalt carbide may result in a decrease in the rate of cobalt catalyst consumption, thereby increasing the efficiency and productivity of the hydroformylation reaction. Suitably, the reduction in the formation of cobalt carbide in the process of the present invention may decrease the amount of cobalt carbide deposited on the internal surfaces of the production facility. Consequently, an increase in efficiency may be achieved.

Typically, during a hydroformylation reaction a cobalt catalyst may decompose to a minor extent to form precipitates of metallic cobalt. Although any decomposition of the cobalt catalyst represents loss of catalyst, the metallic cobalt precipitate is relatively innocuous compared with cobalt carbide formation. Typically, the metallic cobalt precipitates have a relatively small surface area compared with cobalt carbide having the same weight of cobalt and unlike cobalt carbide they typically do not agglomerate and cause the same problems of deposition on the internal surfaces of the production facility. However, although only theory, it is believed that the metallic cobalt precipitates may absorb carbon monoxide from the reaction mixture and promote the dissociation of the carbon monoxide to form cobalt carbide. It is believed that the additive used in the process of the present invention is absorbed by the metallic cobalt precipitate in preference to carbon monoxide, thereby suppressing the absorption of carbon monoxide and the formation of cobalt carbide in the reaction mixture.

The additive may be an inorganic compound which includes a sulfur atom, preferably in an anion.

A preferred inorganic sulfur-containing additive is any sulfur-containing compound that is capable of forming a sulfide anion ($S^{2-}$) in the reaction mixture, able to be absorbed, preferably in preference to carbon monoxide, by the metallic cobalt precipitate. Such additives may include a sulfide anion ($S^{2-}$) per se, for example an inorganic sulfide such as sodium sulfide. Alternatively, or additionally, such additives include those compounds which do not include a sulfide anion ($S^{2-}$) per se, but are capable of generating a sulfide anion during the hydroformylation reaction, for example sodium hydrogen sulfide.

Thus, preferred inorganic sulfur-containing additives include: metal sulfides, preferably of empirical formula $M_xS_y$ where M is a metal cation and either x is 1 or 2 and y is 1, or x is 2 and y is, 3; metal hydrogen sulfides, preferably of empirical formula $M(SH)_z$ where M represents a metal cation and z is 1, 2 or 3; and hydrogen sulfide. Preferably x is 1 or 2 and y is 1. Preferably z is 1 or 2. Suitably, the metal cation M is selected from alkali and alkaline earth metals; preferably from sodium, potassium, calcium, magnesium and zinc. Most preferably the metal cation is potassium, or especially, sodium.

Especially preferred inorganic sulfur-containing additives include sodium sulfide ($Na_2S$), hydrogen sulfide and, especially, sodium hydrogen sulfide (NaHS).

The additive may be an organic sulfur-containing compound. Preferred organic sulfur-containing additives include thiols, disulfides, thioethers and thiophene compounds. A preferred thiol is represented by the general formula $R^5$—SH, where $R^5$ represents lower alkyl or aryl as defined hereinafter. A preferred disulfide is represented by the general formula $R^6$—SS—$R^7$, wherein $R^6$ and $R^7$ each independently represents lower alkyl or aryl. In highly preferred disulfides both $R^6$ and $R^7$ represent lower alkyl. A preferred thioether is represented by the general formula $R^6$—S—$R^7$ wherein $R^6$ and $R^7$ each independently represent lower alkyl or aryl. Highly preferred thioethers include di(lower alkyl) sulfides, especially dimethyl sulfide. A preferred thiophene compound is thiophene itself.

Highly preferred organic sulfur-containing additives include dimethylsulfide and thiophene.

An especially preferred sulfur-containing additive is sodium hydrogen sulfide which generates a sulfide anion ($S^{2-}$) during the hydroformylation reaction.

The term lower alkyl includes linear or branched, cyclic or acyclic, groups of up to 20 carbon atoms, which may be interrupted by oxygen. Preferably no more than five oxygen atoms are present in an alkyl chain. More preferably there are no oxygen atoms present in the alkyl chain, the chain (or backbone) being made up of only carbon atoms. Optional substituents may include, for example, halo, cyano, hydroxyl, $C_1$–$C_4$ alkoxy, $C_1$–$C_4$ haloalkoxy, ($C_1$–$C_4$ alkoxy) carbonyl, amino and mono- or di- $C_1$–$C_4$ alkylamino groups. When an alkyl group is substituted it preferably has 1–3 substituents. Preferably, however, an alkyl group is unsubstituted. Lower alkyl groups may favourably have up to 16 carbon atoms, preferably up to 10, more preferably up to 6, and most preferably up to 4. Acyclic alkyl groups are preferred. Linear groups are preferred. Preferred lower alkyl groups include the propyl and butyl groups, especially n-propyl and n-butyl, and, most preferred, ethyl and, especially methyl.

The term aryl includes six to ten-membered carbocyclic aromatic groups, such as phenyl and naphthyl, which groups are optionally substituted by one or more substituents, for example 1–3 substituents, preferably selected from halo, cyano, nitro, lower alkyl, lower haloalkyl, $OR^8$, $C(O)R^8$, $C(O)OR^8$ where $R^8$ represents a lower alkyl or aryl group. Preferred aryl groups are unsubstituted. Highly preferred aryl groups are phenyl and tolyl.

The term halo includes fluoro, chloro, bromo and iodo.

Preferably the additive provides sulfur in an amount of up to about 80 ppm (parts per million), preferably up to about 50 ppm, more preferably up to about 30 ppm, and most preferably up to about 15 ppm, by weight of the total reaction mixture.

Preferably the additive provides sulfur in an amount of at least about 5 ppm, most preferably at least about 10 ppm, by weight of the total reaction mixture.

Preferably, a process in accordance with the invention, including a sulfur-containing additive, produces less than 50% of the cobalt carbide, over a given time period, compared with that produced by the corresponding hydroformylation process in the absence of the additive; and more preferably less than 25% (weight/weight).

Preferably, the additive does not substantially affect the activity and/or stability of the cobalt catalyst in the hydroformylation process. In other words, the rate of hydroformylation with the inclusion of the additive in the reaction mixture is substantially the same as the rate of hydroformylation without the inclusion of the additive in the reaction mixture, under identical reaction conditions. By "substantially the same" we mean that, preferably, the rate of hydroformylation with the inclusion of the additive in the reaction mixture is at least 90% of the rate of hydroformylation without the additive.

Preferably, the stability of the cobalt catalyst during the hydroformylation reaction with the inclusion of the additive remains substantially the same as the stability of the cobalt catalyst during a corresponding hydroformylation reaction without the inclusion of the additive under identical reaction conditions. Suitably, the stability of the cobalt catalyst may be determined by methods well known to those skilled in the art, for example infra-red spectrophotometry or elemental analysis, by monitoring the amount of cobalt lost from a known concentration of a catalyst during the hydroformylation of a known concentration of an olefinic compound, at a specific reaction temperature and specific pressure of hydrogen and carbon monoxide.

Preferably the cobalt catalyst comprises cobalt in complex combination with carbon monoxide and an organophosphine. By the term "complex combination" we mean a coordination compound formed by the union of one or more carbon monoxide and organophosphine molecules with one or more cobalt atoms. In its active form the preferred cobalt catalyst contains the cobalt component in a reduced valence state.

Suitable organophosphine ligands include, for example, those having a trivalent phosphorus atom having one available or unshared pair of electrons. Any essentially organic derivative of trivalent phosphorus with the foregoing electronic configuration is a suitable ligand for the cobalt catalyst. It thus will operate as a ligand in forming the desired cobalt catalyst.

Organic radicals of any size and composition may be bonded to the phosphorus atom. For example the organophosphine ligand may comprise a trivalent phosphorus having aliphatic and/or cycloaliphatic and/or heterocyclic and/or aromatic radicals satisfying its three valences. These radicals may contain a functional group such as carbonyl, carboxyl, nitro, amino, hydroxy, saturated or unsaturated carbon-to-carbon linkages, and saturated and unsaturated non-carbon-to-carbon linkages.

It is also suitable for an organic radical to satisfy more than one of the valences of the phosphorus atom, thereby forming a heterocyclic compound with a trivalent phosphorus atom. For example, an alkylene radical may satisfy two phosphorus valences with its two open valences and thereby form a cyclic compound. Another example would be an alkylene dioxy radical that forms a cyclic compound where the two oxygen atoms link an alkylene radical to the phosphorus atom. In these two examples, the third phosphorus valence may be satisfied by any other organic radical.

Another type of structure involving trivalent phosphorus having an available pair of electrons is one containing a plurality of such phosphorus atoms linked by organic radicals. This type of a compound is typically called a bidentate ligand when two such phosphorus atoms are present, a tridentate ligand when three such phosphorus are present, and so forth.

Examples of suitable cobalt catalysts for use in the process of the present invention and their methods of preparation are disclosed in U.S. Pat. Nos. 3,369,050, 3,501,515, 3,448,158, 3,448,157, 3,420,898 and 3,440,291, all of which are incorporated herein by reference. Preferably, the cobalt catalyst is substantially homogeneous with the reaction mixture.

Preferred cobalt catalysts for use in the process of the present invention are those which include an organic tertiary phosphine ligand, especially a bicyclic heterocyclic tert-phosphine ligand, preferably as disclosed in U.S. Pat. No. 3,501,515. Representative examples of such ligands include:

9-hydrocarbyl-9-phosphabicyclo[4,2,1]nonane;
9-aryl-9-phosphabicyclo[4,2,1]nonane,
such as 9-phenyl-9-phosphabicyclo[4,2,1]nonane;
(di)alkyl-9-aryl-9-phosphabicyclo[4,2,1]nonane,
such as 3,7-dimethyl-9-phenyl-9-phosphabicyclo[4,2,1]-nonane and 3,8-dimethyl-9-phenyl-9-phosphabicyclo[4,2,1]nonane;
9-alkyl-9-phosphabicyclo[4,2,1]nonane,
such as 9-octadecyl-9-phosphabicyclo[4,2,1]nonane,
9-hexyl-9-phosphabicyclo[4,2,1]nonane,
9-eicosyl-9-phosphabicyclo[4,2,1]nonane, and
9-triacontyl-9-phosphabicyclo[4,2,1]nonane;
9-cycloalkyl-9-phosphabicyclo[4,2,1]nonane,
such as 9-cyclohexyl-9-phosphabicyclo[4,2,1]nonane and
9-(1-octahydropentalyl)-9-phosphabicyclo[4,2,1]nonane;
9-cycloalkenyl-9-phosphabicyclo[4,2,1]nonane,
such as 9-cyclooctenyl-9-phosphabicyclo[4,2,1]nonane;
9-hydrocarbyl-9-phosphabicyclo [3,3,1] nonane;
9-aryl-9-phosphabicyclo[3,3,1]nonane,
such as 9-phenyl-9-phosphabicyclo[3,3,1]nonane;
9-alkyl-9-phosphabicyclo[3,3,1]nonane,
such as 9-hexyl-9-phosphabicyclo[3,3,1]nonane, and
9-eicosyl-9-phosphabicyclo[3,3,1]nonane.

A particularly preferred ligand includes a tricarbonyl-9-eicosyl-9-phosphabicyclo nonane compound. A particularly preferred catalyst includes a derivative thereof with cobalt.

Cobalt catalysts can be prepared by a diversity of methods, for example, as disclosed in U.S. Pat. Nos. 3,369,500, 3,501,515, 3,448,157, 3,420,898 and 3,440,291, which disclosures are herein incorporated by reference. A convenient method is to combine a cobalt salt, organic or inorganic, with the desired phosphine ligand, for example, in liquid phase followed by reduction and carbonylation. Suitable cobalt salts comprise, for example, cobalt carboxylates such as acetates, octanoates, etc. as well as cobalt salts of mineral acids such as chlorides, fluoride, sulfates, sulfonates, etc. as well as mixtures of one or more of these cobalt salts. The valence state of the cobalt may be reduced and the cobalt-containing complex formed by heating the solution in an atmosphere of hydrogen and carbon monoxide. The reduction may be performed prior to the use of the catalysts or it may be accomplished simultaneously with the hydroformylation process in the hydroformylation zone. Alternatively, the catalysts can be prepared from a carbon monoxide complex of cobalt. For example, it is possible to start with dicobalt octacarbonyl and, by mixing this substance with a suitable phosphine ligand, the ligand replaces one or more of the carbon monoxide molecules, producing the desired catalyst.

The ratio of catalyst to the olefinic compound to be hydroformylated may vary widely. It may be varied to achieve a substantially homogeneous reaction mixture. Solvents are therefore not required. However, solvents which are inert, or which do not interfere to any substantial degree with the desired hydroformylation reaction under the conditions employed, may be used. Saturated liquid hydrocarbons, for example, may be used as solvent in the process, as well as alcohols, ethers, acetonitrile, sulfolane, and the like. Molar ratios of catalyst to the olefinic compound in the reaction zone at any given instant between about 1:1000 and about 10:1 are found to be satisfactory; a higher or lower ratio of catalyst to olefinic compound may, however, be used, but in general the preferred ratio is less than 1:1.

The ratio of hydrogen to carbon monoxide may vary widely. In general, a mole ratio of at least about 1, hydrogen to carbon monoxide, may be employed. Suitably ratios of hydrogen to carbon monoxide may be within the range of from about 1 to about 10. Higher or lower ratios may, however, be employed. The ratio of hydrogen to carbon monoxide employed may be adjusted according to the nature of the reaction product desired. For example, in making primarily an aldehyde product, only one mole of hydrogen per mole of carbon monoxide reacts with the olefinic compound. When an alcohol is the preferred product of the process of the present invention, two moles of hydrogen and one mole of carbon monoxide react with each mole of olefinic compound. The use of ratios of hydrogen to carbon monoxide which are somewhat lower than those defined by these values are generally preferred.

The process of the present invention may be carried out at various pressures. Consequently, hydroformylation in accordance with the process of the present invention may typically be carried out at pressures below about $7 \times 10^6$ Pa, to as low as about $1 \times 10^5$ Pa. The process of the present invention is, however, not limited in its applicability to the lower pressures and pressures in the broad range from about $1 \times 10^5$ Pa up to about $14 \times 10^6$ Pa and in some cases up to about $20 \times 10^6$ Pa, or even higher, may be employed. Typically, the specific pressure used may be adjusted according to the charge and catalyst employed. In general, pressures in the range of from about $2 \times 10^6$ Pa to about $10 \times 10^6$ Pa and particularly in the range of from about $2.7 \times 10^6$ Pa to about $9 \times 10^6$ Pa are preferred.

Temperatures employed in the process of the invention may generally be at least about 100° C., preferably in the range from about 100° C. to about 300° C. and more preferably about 150° C. to about 210° C., a temperature of about 200° C. being generally satisfactory. Somewhat higher or lower temperatures may, however, be used within the scope of the invention.

Depending upon the charge and cobalt catalyst employed, the present invention may provide the direct, single stage hydroformylation of an olefinic compound to yield a reaction product wherein the alcohols predominate over the aldehydes. By selection of reaction conditions, charge and cobalt catalyst as described herein it may be possible to obtain greater than or equal to about 80% of straight chain alcohols, rather than various branched isomers from the hydroformylation of olefinic compounds. By varying the operating conditions as described hereinbefore the ratio of aldehydes to alcohols product may be varied.

The process of the present invention may be generally applicable to the hydroformylation of any aliphatic or cycloaliphatic compound having at least one olefinic carbon-to-carbon bond. Thus, it may be applied to the hydroformylation of olefinic compounds comprising olefinically unsaturated compounds having, for example, from 2 to 19 carbons, to produce reaction mixtures predominating in aliphatic aldehydes and alcohols having one more carbon atom than the starting olefinic compound. Mono-olefinic compounds, such as ethylene, propylene, butylenes, amylenes, hexylenes, heptylenes, octylenes, nonylenes, decylenes, undecylenes, dodecylenes, tridecylenes, tetradecylenes, pentadecylenes, hexadecylenes, heptadecylenes, octade-cylenes, nonadecylenes, and their homologues, are examples of suitable unsaturated compounds which may be hydroformylated in the process of the present invention. Suitable unsaturated compounds include both branched and straight-chain compounds having one or more olefinic sites. When two or more double bonds are present these may be conjugated, as in 1,2-hexadiene. In the case of polyolefinic compounds, it is possible to hydroformylate only one of the olefinic sites or several or all of these sites. The unsaturated carbon-to-carbon olefinic linkages may be between terminal and their adjacent carbon atoms, as in 1-pentene, or between internal chain carbon atoms, as in 4-octene.

Preferably an olefinic compound used in the process is a mono-olefinic compound.

Preferably an olefinic compound used in the process has an olefinic linkage between a terminal carbon atom and its adjacent carbon atom.

Hydroformylation of macromolecular materials involving acyclic units of the above types, such as polydiolefinic compounds, for example polybutadiene, as well as copolymers of olefinic and diolefinic compounds, for example styrene-butadiene copolymer, may also be accomplished by the process of the present invention.

Cyclic compounds are equally suitable for use in the process of the present invention. Suitable cyclic compounds include, for example, unsaturated alicyclic compounds such as the cyclic olefinic compounds containing carbon-to-carbon unsaturation, such as cyclopentene, cyclohexene, and cycloheptene. Also included in this category are, for example, the terpenes and fused-ring polycyclic olefinic compounds, such as 2,5-bicyclo(2,2,1)heptadiene, 1,4,4a,5, 8,8a-hexahydro-1,4,5,8-dimethanonaphthalene and the like.

The process of this invention may be used to hydroformylate olefinic carbon-to-carbon linkages of hydrocarbons but may also be used for non-hydrocarbons. Thus, it is possible to hydroformylate olefinically unsaturated alcohols, epoxides, aldehydes, and acids to corresponding alcohols, aldehydes, and acids containing an aldehyde or hydroxy group on one of the carbon atoms previously involved in the olefinic bond of the starting material. The following are a few non-limiting examples of different types of olefinic compounds that may be hydroformylated by the process of the present invention and the products obtained thereby:

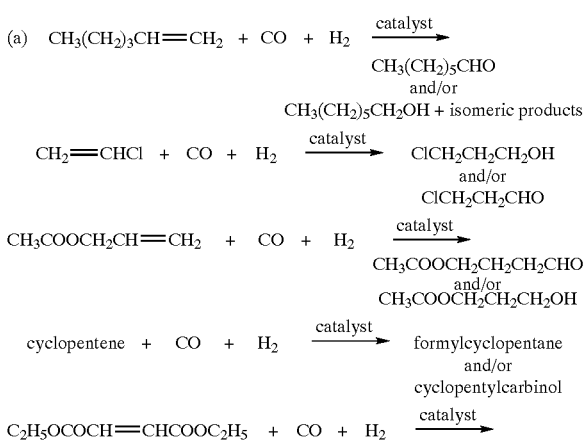

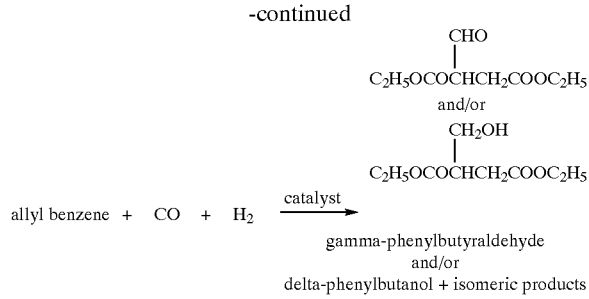

The olefinic charge to the process of the invention may comprise one, two, or more of the suitable olefinic compounds described herein. Olefinic compounds may be hydroformylated under the conditions defined above to produce mixtures of aldehydes and alcohols in which the alcohols predominate.

The present invention may thus provide the direct, single stage hydroformylation of olefinic compounds, preferably mono-olefinic compounds, and especially mono-olefins, having, for example, from 2 to 19 carbon atoms per molecule, preferably to produce predominantly terminal alcohols having 5 to 20 carbon atoms per molecule, respectively. Olefinic fractions, such as, for example, polymeric olefinic fractions, cracked wax fractions, and the like, containing substantial proportions of olefinic compounds, may be readily hydroformylated to fractions of hydroformylated products comprising mixtures of predominantly terminal aldehydes and alcohols having one more carbon than the olefinic compounds in the charge and wherein these alcohols are the predominant reaction product. Such suitable feeds consisting of olefinic fractions include, for example, $C_7$, $C_8$, $C_9$, $C_{10}$ and higher olefinic fractions as well as olefinic hydrocarbon fractions of wider boiling ranges such as $C_7$–$C_9$, $C_{10}$–$C_{13}$, $C_{14}$–$C_{17}$ olefinic hydrocarbon fractions and the like. In broad terms $C_8$–$C_{16}$ olefinic compounds, in particular $C_8$–$C_{16}$ olefinic hydrocarbons, are preferred.

It will be appreciated that under the above-defined conditions, the olefinic charge may react with carbon monoxide and hydrogen and may form reaction products comprising aldehydes and/or alcohols having one more carbon atom per molecule than the olefin charged.

The proportions in which reactants are fed to the reaction zone may vary over relatively wide limits, for example, from about 1 to about 5 molar amounts of an olefinic compound as described hereinbefore may be reacted with from about 1 to about 12 moles of hydrogen and about 1 to about 7 moles of carbon monoxide. Sufficient amounts of olefinic compound are however included in the feed to the reaction zone.

Admixtures of promoters, stabilizers and the like may also be included in the process of the present invention. For example, minor amounts of phenolic stabilizers such as hydroquinone and alkaline agents such as hydroxides of alkali metals, for example NaOH and KOH, may be added to the reaction zone.

The reaction mixtures obtained may be subjected to suitable catalyst and product separating means comprising one or more steps, for example, stratification, solvent extraction, distillation, fractionation, adsorption, etc. The method of product and catalyst separation preferably employed may be varied according to the complex and reactants charged. Catalyst or components thereof, as well as unconverted charge, and solvent, when employed, may be recycled in part or entirety to the reaction zone.

The preformed cobalt catalyst, or separate components of the catalyst capable of producing the complex in situ in the reaction zone, may be added to material separated from the reactor which is being recycled to the reaction zone. A part of an alcoholic reaction product may, if desired, be recycled to the reaction zone to function as solvent and/or diluent and/or suspending medium for the catalyst, the catalyst components, and the like, passing to the reaction zone. A part or all of an aldehyde product may optionally be recycled to the reaction zone or may be, subjected to hydroformylation conditions in a second and separate reaction zone in the presence of a cobalt catalyst. The cobalt catalyst used in the second hydroformylation step need not be the same as that used in the first step.

According to a further aspect, the present invention provides the use of an additive as defined hereinbefore for suppressing the formation of cobalt carbide in a reaction employing a cobalt complex catalyst.

The invention will be further described by way of the following non-limiting examples.

Batch and pilot plant experiments were performed to determine the stability of a cobalt/phosphine catalyst in a hydroformylation reaction and the type of catalytic decomposition products.

EXAMPLE 1

Preparation of a Standard Cobalt Catalyst Solution (Preliminary)

A phosphine ligand, (268 g, 0.63 mol) 9-eicosyl-9-phosphabicyclononane, a commercial mixture from Shell, and hereinafter called the P-ligand, was melted at 60° C. and charged into a 1 liter glass bottle. To this was added 298 g of a 10 wt % cobalt solution of cobalt octoate in 2-ethyl hexanol (equivalent to 0.48 mol of cobalt), followed by 268 g of Neodol-23™, a commercial mixture of $C_{12}$ and $C_{13}$ linear detergent alcohols available from Shell. The solution was stirred for two hours at 60° C. and used as stock solution for the following batch experiments. The cobalt catalyst solution was stored at ambient temperature and pressure.

A 1.3 wt % stock solution of potassium hydroxide in Neodol-23™ was prepared by dissolving 5 g of-powdered KOH in 386 g of Neodol-23™ at 50° C. This solution was stored at ambient temperature and pressure.

EXAMPLE 2

Batch Experiment to Determine the Stability of the Cobalt Catalyst and the Type of Decomposition Product without an Additive (Comparative)

A stainless steel autoclave, equipped with stirrer, temperature and pressure control, was charged with 100 g of Neodol-23™ and 30 g of the 1.3 wt % solution of KOH in Neodol-23™ of Example 1. After flushing the system with nitrogen and syngas to remove residual oxygen, the autoclave was heated to 197° C. and pressurized with $H_2$ and CO (inlet ratio $H_2$/CO=1.8) to a pressure of $6 \times 10^6$ Pa. Subsequently, 30 g of the cobalt catalyst solution of Example 1 was injected to start the experiment.

After 5 minutes at 197° C. and 6×10⁶ Pa syngas pressure to allow formation of the active catalyst, a reference sample was taken and analysed by infra-red spectrophotometry to determine the composition and cobalt concentration of the catalyst.

The autoclave was kept at 197° C. and 6×10⁶ Pa syngas pressure, while at regular intervals samples were withdrawn to determine the cobalt concentration by infra-red spectrophotometry. After 150 hours more than 50% of the cobalt catalyst had disappeared as determined by infra-red and the autoclave was cooled to room temperature and depressurised. The liquid was decanted and the solids were collected and analysed by X-ray diffraction to determine the composition of the solid residue. The solid residue was shown to be almost pure cobalt carbide. The first-order-decay rate constant of the cobalt catalyst, determined from the decrease in cobalt concentration by infra-red spectrophotometry was $0.006\ h^{-1}$.

EXAMPLE 3

Batch Experiment to Determine the Stability of the Cobalt Catalyst and the Type of Decomposition Product without an Additive, but in the Presence of Added Cobalt Carbide (Comparative)

A stainless steel autoclave, equipped with stirrer, temperature and pressure control, was charged with 100 g of Neodol-23™ and 30 g of the 1.3 wt % solution of KOH in Neodol-23™ of Example 1. In this particular experiment 2 g of cobalt carbide in powder form was also added to the autoclave. After flushing the system with nitrogen and syngas to remove residual oxygen, the autoclave was heated to 197° C. and pressurized with $H_2$ and CO (inlet ratio $H_2/CO=1.8$) to a pressure of 6×10⁶ Pa. Subsequently, 30 g of the standard catalyst solution of Example 1 was injected to start the experiment.

After 5 minutes at 197° C. and 6×10⁶ Pa syngas pressure to allow formation of the active catalyst, a reference sample was taken and analysed by infra-red spectrophotometry to determine the composition and cobalt concentration of the catalyst.

The autoclave was kept at 197° C. and 6×10⁶ Pa syngas pressure, while at regular time intervals samples were withdrawn to determine the cobalt concentration by infra-red spectrophotometry. After 18 hours more than 50% of the cobalt catalyst had disappeared and the autoclave was cooled to ambient temperature and depressurised. The liquid was decanted and the solids were collected and analysed by X-ray diffraction to determine the composition of the solid residue. The solid residue was shown to be almost pure cobalt carbide. The first-order-decay rate constant of the cobalt catalyst, determined from the decrease in cobalt concentration by infra-red, was $0.062\ h^{-1}$.

The experiment demonstrates that the presence of cobalt carbide in the reaction mixture dramatically affects the stability of the cobalt catalyst, as the first order decay rate constant for the cobalt catalyst with added cobalt carbide in the reaction is $0.062\ h^{-1}$, whereas the first order decay rate constant of the catalyst without cobalt carbide is $0.006\ h^{-1}$ (see Example 2).

EXAMPLE 4

Batch Experiment to Determine the Stability of the Cobalt Catalyst and the Type of Decomposition Product in the Presence of 50 ppm wt Thiophene Additive A stainless steel autoclave, equipped with stirrer, temperature and pressure control, was charged with 90 g of Neodol-23™ and 35 g of a 1.3 wt % solution of KOH in Neodol-23 ™ of Example 1 and 0.022 g of thiophene. After flushing the system with nitrogen and syngas to remove residual oxygen, the autoclave was heated to 192° C. and pressurized with $H_2$ and CO (inlet ratio $H_2/CO=1.8$) to a pressure of 6×10⁶ Pa. Subsequently 30 g of the standard catalyst solution of Example 1 was injected to start the experiment.

After 5 minutes at 192° C. and 6×10⁶ Pa syngas pressure to allow formation of the active catalyst, a reference sample was taken and analysed by infra-red spectrophotometry to determine the composition and cobalt concentration of the catalyst.

The autoclave was kept at 192° C. and 6×10⁶ Pa syngas pressure, while at regular intervals samples were withdrawn to determine the cobalt concentration by infra-red. After 100 hours more than 50% of the cobalt catalyst had disappeared as determined by infra-red and the autoclave was cooled to room temperature and depressurised. The liquid was decanted and the solids were collected and analysed by X-ray diffraction to determine the composition of the solid residue. The solid residue was shown to be almost pure cobalt metal. The first order decay rate constant of the cobalt catalyst, determined from the decrease in cobalt concentration by infra-red spectrophotometry, was $0.008\ h^{-1}$.

This experiment shows that by addition of a sulfur-containing compound the undesired formation of cobalt carbide is prevented and the more desirable cobalt metal is formed. By comparing the first order decay rate constant of the cobalt catalyst for this Example with that of Example 2, it is evident that the sulfur-containing additive has little detrimental effect on the stability of the cobalt catalyst.

Additional batch experiments, with different additives, varying concentrations of additives, and at different temperatures, referred to as Experiments 5 to 29 in Table 1 below, were performed as described in the preceding examples to determine the efficiency of various additives at suppressing cobalt carbide formation and the effect the additives have on the stability of the cobalt catalyst. The results are presented in Table 1 below. The symbol P-ligand/Co denotes the cobalt catalyst solution as described in Example 1. The symbol $Co_xC$ denotes cobalt carbide, whether $Co_2C$ or $CO_3C$, or both in admixture; the structure/empirical formula is not significant and was not determined.

TABLE 1

| Type | T (° C.) | P-ligand/Co | K/Co | S-source | [S]ppmw | deposits | decay rate (h$^{-1}$) |
|---|---|---|---|---|---|---|---|
|  | 200 | 1.3 | 0.4 | none |  | Co$_x$C | 0.010 |
| 6 | 210 | 1.3 | 0.4 | none |  | Co$_x$C | 0.031 |
| 7 | 192 | 1.3 | 0.5 | none |  | Co$_x$C | 0.016 |
| 8 | 210 | 1.2 | 0.4 | none |  | Co$_x$C | 0.27 |
| 9 | 210 | 1.3 | 0.4 | dimethyldisulfide | 1 | Co$_x$C | 0.040 |
| 10 | 210 | 1.3 | 0.4 | dimethyldisulfide | 5 | Co$_x$C and Co | 0.055 |
| 11 | 210 | 1.3 | 0.4 | dimethyldisulfide | 10 | Co$_x$C and Co | 0.040 |
| 12 | 210 | 1.3 | 0.4 | dimethyldisulfide | 15 | Co$_x$C and Co | 0.038 |
| 13 | 210 | 1.3 | 0.4 | dimethyldisulfide | 20 | Co$_x$C and Co | 0.028 |
| 14 | 210 | 1.3 | 0.4 | dimethyldisulfide | 100 | Co | 0.9 |
| 15 | 192 | 1.3 | 0.5 | dimethyldisulfide | 50 | Co | 0.016 |
| 16 | 210 | 1.3 | 0.4 | thiophene | 10 | Co$_x$C and Co | 0.05 |
| 17 | 210 | 1.3 | 0.4 | thiophene | 25 | Co$_x$C and Co | 0.05 |
| 18 | 210 | 1.3 | 0.4 | thiophene | 50 | Co$_x$C and Co | 0.05 |
| 19 | 192 | 1.3 | 0.5 | thiophene | 50 | Co | 0.008 |
| 20 | 210 | 1.3 | 0.4 | sodium sulfide | 11 | Co$_x$C and Co | 0.027 |
| 21 | 210 | 1.3 | 0.4 | sodium sulfide | 50 | Co$_x$C and Co | 0.13 |
| 22 | 192 | 1.3 | 0.5 | sodium sulfide | 25 | Co$_x$C and Co | 0.024 |
| 23 | 192 | 1.3 | 0.5 | sodium sulfide | 50 | Co | 0.056 |
| 24 | 192 | 1.3 | 0.5 | Sodium hydrogen sulfide | 25 | Co$_x$C and Co | 0.019 |
| 25 | 192 | 1.3 | 0.05 | Sodium hydrogen sulfide | 50 | Co | 0.024 |
| 26 | 210 | 1.3 | 0.4 | thianthrene | 25 | Co$_x$C and Co | 0.039 |
| 27 | 210 | 1.3 | 0.4 | thianthrene | 50 | Co$_x$C and Co | 0.031 |
| 28 | 210 | 1.3 | 0.4 | dibenzothiophene | 25 | Co$_x$C and Co | 0.030 |
| 29 | 210 | 1.3 | 0.4 | dibenzothiophene | 50 | Co$_x$C and Co | 0.033 |

Experiment 30

Continuous Experiment to Determine the Stability of the Cobalt Catalyst and the Type of Decomposition Product without an Additive (Comparative)

A reaction zone, consisting of four autoclaves in series operated 192° C. and 5×10$^6$ Pa syngas (inlet ratio H$_2$/CO= 1.7), was fed with a continuous feed stream of olefin NEODENE™, from Shell, catalyst components (cobalt octoate, P-ligand as for Example 1, KOH), fresh syngas and catalyst recycle stream. After depressurisation, the product alcohols, formed by hydroformylation of the olefin feed stream, and the catalyst dissolved in heavy by-products were separated via a short-path distillation. The heavy-bottom stream containing the cobalt catalyst was recycled back to the autoclaves. The experiment was operated in a continuous mode.

Feed rates of the catalyst components were adjusted to maintain the targeted steady-state catalyst concentration. and composition: 0.25 wt % cobalt, P-ligand/Co=1.3 and KOH/Co=0.5.

Cobalt carbide 30 g in powder form was placed in autoclaves 1 and 3 and the run was continued for 600 hours to determine a reference point. After 600 hours the autoclaves were cooled to ambient temperature and depressurised. The solids, both the on-purpose added carbide and the fresh deposits, were collected and analysed by X-ray diffraction. Operation at these conditions led to formation of fresh cobalt carbide depositions on the on-purpose added cobalt carbide sample material. The catalyst decomposition rate, a measure for catalyst stability, was determined to be 0.075 g Co/kg of hydroformylation products produced over the 600 hour test period.

Experiment 31

Continuous Experiment to Determine the Stability of the Cobalt Catalyst and the Type of Decomposition Product with a Sulfur-containing Additive A reaction was carried out as described in Example 30, except that sodium sulfide was also added.

Feed rates of the catalyst components were adjusted to maintain the targeted steady-state catalyst concentration and composition: 0.25 wt % cobalt, P-ligand/Co=1.3 and KOH/Co=0.5.

Sodium sulfide was fed to the reactor on a continuous basis to maintain 10 ppm sulfur concentration in the reaction mixture.

Cobalt carbide (30 g) in powder form was placed in reactors 1 and 3, and the run was continued for 600 hours to determine a reference point. After 600 hours the reactors were cooled to room temperature and depressurised. The solids, both the on-purpose added carbide and the fresh deposits, were collected and analysed by X-ray diffraction. Operation at these conditions led to formation of fresh cobalt metal on the on-purpose added cobalt carbide sample material. The catalyst decomposition rate was determined to be 0.106 g Co/kg of hydroformylation products produced over the 600 hour test period.

The results of Experiment 30 and 31 demonstrate that the addition of a sulfur-containing additive suppresses the formation of cobalt carbide and results in the formation of the more desirable cobalt metal.

EXAMPLES 32–40

Continuous Experiments to Determine the Stability of the Cobalt Catalyst and the Type of Decomposition Product with a Sulfur-containing Additive Additional continuous experiments with varying concentrations of sodium sulfide as additive were performed to determine their efficiency at suppressing the formation of cobalt catalyst and the effect the additive has on the stability of the cobalt catalyst. All experiments were carried out in the presence of added cobalt carbide, in powder form at 192° C., over an 1800 hour time period, and with other conditions as described in the preceding example 31. Conditions and results are summarised in Table 2 below.

TABLE 2

| Example | S-source | [S]reactors (ppmw) | P-ligand/Co decomp. rate (g Co/kg olefin) | Deposits |
|---|---|---|---|---|
| 32 | none |  | 0.115 | $Co_xC$ |
| 33 | none |  | 0.087 | $Co_xC$ |
| 33 | none |  | 0.070 | $Co_xC$ |
| 35 | sodium sulfide | <5 | 0.050 | $Co_xC$ |
| 36 | Sodium sulfide | 10 | 0.106 | Co |
| 37 | sodium sulfide | 15 | 0.050 | Co |
| 38 | Sodium sulfide | 18 | 0.013 | Co |
| 39 | Sodium sulfide | 30 | 0.064 | Co |
| 40 | sodium sulfide | 40 | 0.160 | Co |

The results demonstrate that in a reaction mixture which comprises a sodium sulfide additive which provides a weight of sulfur greater than 5 parts per million of the weight of the reaction mixture then the formation of cobalt carbide is suppressed and cobalt metal is formed. Moreover, the stability of the cobalt catalyst is not significantly affected.

We claim:

1. A hydroformylation process comprising reacting a compound having at least one olefinic carbon-to-carbon bond with hydrogen and carbon monoxide in the presence of a homogeneous cobalt catalyst and a sulfur-containing additive that is capable of forming a sulfide anion ($S^{2-}$) in the reaction mixture and which suppresses the formation of cobalt carbide during the reaction.

2. The process of claim 1 wherein the additive is an inorganic sulfur-containing additive.

3. The process of claim 2 wherein the inorganic sulfur-containing additive is selected from the group consisting of metal sulfides, metal hydrogen sulfides and hydrogen sulfide.

4. The process of claim 3 wherein the inorganic sulfur-containing additive is a metal sulfide having the general formula $M_xS_y$ wherein M is a metal cation and: (i) x is 1 or 2 and y is 1; or (ii) x is 2 and y is 3.

5. The process of claim 4 wherein M is a cation of a metal selected from the group consisting of sodium, potassium, calcium, magnesium and zinc.

6. The process of claim 3 wherein the inorganic sulfur-containing additive is a metal hydrogen sulfide having the general formula $M(SH)_z$ wherein M is a metal cation and z is 1, 2 or 3.

7. The process of claim 6 wherein M is a cation of a metal selected from the group consisting of sodium, potassium, calcium, magnesium and zinc.

8. The process of claim 3 wherein the inorganic sulfur-containing additive is selected from the group consisting of sodium hydrogen sulfide, sodium sulfide, and hydrogen sulfide.

9. The process of claim 2 wherein the inorganic sulfur-containing additive is hydrogen sulfide.

10. The process of claim 1 wherein the additive is an organic sulfur-containing compound.

11. The process of claim 10 wherein the organic sulfur-containing compound has a thiol functional group.

12. The process of claim 11 wherein the organic sulfur-containing compound has the general formula $R^5$—SH, wherein $R^5$ is a lower alkyl or aryl.

13. The process of claim 10 wherein the organic sulfur-containing compound has a disulfide linkage.

14. The process of claim 13 wherein the organic sulfur-containing compound has the general formula $R^6$—SS—$R^7$, wherein $R^6$ and $R^7$ each independently represent a lower alkyl or aryl.

15. The process of claim 10 wherein the organic sulfur-containing compound has a thioether linkage.

16. The process of claim 15 wherein the organic sulfur-containing compound has the general formula $R^6$—S—$R^7$, wherein $R^6$ and $R^7$ each independently represent a lower alkyl or aryl.

17. The process of claim 16 wherein the organic sulfur-containing compound is dimethylsulfide.

18. The process of claim 10 wherein the organic sulfur-containing compound comprises a thiophene compound.

19. The process of claim 10 wherein the organic sulfur-containing compound is selected from the group consisting of thiophene and dimethyldisulfide.

20. The process of claim 1 wherein the compound having at least one olefinic carbon-to-carbon bond is a mono-olefinic compound.

21. The process of claim 1 wherein the compound having at least one olefinic carbon-to-carbon bond has an olefinic linkage between a terminal carbon atom and its adjacent carbon atom.

22. The process of claim 20 wherein the compound having at least one olefinic carbon-to-carbon bond is a mono-olefinic compound having from 2 to 19 carbon atoms per molecule.

23. The process of claim 1 wherein the additive does not substantially affect the stability and/or activity of the cobalt catalyst.

24. The process of claim 2 wherein the additive does not substantially affect the stability and/or activity of the cobalt catalyst.

25. The process of claim 10 wherein the additive does not substantially affect the stability and/or activity of the cobalt catalyst.

26. The process of claim 1 wherein the additive provides a sulfur amount of up to about 80 parts per million by weight of the total reaction mixture.

27. The process of claim 26 wherein the additive provides a sulfur amount of up to about 50 parts per million by weight of the total reaction mixture.

28. The process of claim 2 wherein the additive provides a sulfur amount of up to about 80 parts per million by weight of the total reaction mixture.

29. The process of claim 10 wherein the additive provides a sulfur amount of up to about 80 parts per million by weight of the total reaction mixture.

30. The process of claim 1 wherein the additive provides a sulfur amount of at least about 5 parts per million by weight of the total reaction mixture.

31. The process of claim 30 wherein the additive provides a sulfur amount of at least about 10 parts per million by weight of the total reaction mixture.

32. The process of claim 2 wherein the additive provides a sulfur amount of at least about 5 parts per million by weight of the total reaction mixture.

33. The process of claim 10 wherein the additive provides a sulfur amount of at least about 5 parts per million by weight of the total reaction mixture.

34. The process of claim 1 wherein the cobalt catalyst comprises cobalt in complex combination with at least one carbon monoxide molecule and at least one organophosphine ligand.

35. The process of claim 34 wherein the organophosphine ligand has a trivalent phosphorus atom having one available or unshared pair of electrons.

36. The process of claim 34 wherein the cobalt catalyst comprises a compound of the general formula $Co(CO)_3PL$ wherein PL represents a bicyclic heterocyclic tertiary phosphine ligand.

37. The process of claim 2 wherein the cobalt catalyst comprises cobalt in complex combination with at least one carbon monoxide molecule and at least one organophosphine ligand.

38. The process of claim 37 wherein the cobalt catalyst comprises a compound of the general formula $Co(CO)_3PL$ wherein PL represents a bicyclic heterocyclic tertiary phosphine ligand.

39. The process of claim 10 wherein the cobalt catalyst comprises cobalt in complex combination with at least one carbon monoxide molecule and at least one organophosphine ligand.

40. The process of claim 39 wherein the cobalt catalyst comprises a compound of the general formula $Co(CO)_3PL$ wherein PL represents a bicyclic heterocyclic tertiary phosphine ligand.

41. The process of claim 1 wherein the compound having at least one olefinic carbon-to-carbon bond comprises an olefinic hydrocarbon having up to 19 carbon atoms.

42. The process of claim 2 wherein the compound having at least one olefinic carbon-to-carbon bond comprises an olefinic hydrocarbon having up to 19 carbon atoms.

43. The process of claim 10 wherein the compound having at least one olefinic carbon-to-carbon bond comprises an olefinic hydrocarbon having up to 19 carbon atoms.

44. The process of claim 1 wherein the reaction is performed at a temperature of at least about 100° C. and at a pressure of greater than about $1 \times 10^5$ Pa.

45. The process of claim 44 wherein the pressure is below about $7 \times 10^6$ Pa.

46. The process of claim 1 wherein the temperature is within the range of from about 100° C. to about 300° C.

47. The process of claim 2 wherein the reaction is performed at a temperature of at least about 100° C. and at a pressure of greater than about $1 \times 10^5$ Pa.

48. The process of claim 10 wherein the reaction is performed at a temperature of at least about 100° C. and at a pressure of greater than about $1 \times 10^5$ Pa.

49. The process of claim 1 wherein the sulfur-containing additive produces less than 50% by weight of cobalt carbide compared with that produced in the absence of the additive.

50. A hydroformylation process comprising reacting a compound having at least one olefinic carbon-to-carbon bond with hydrogen and carbon monoxide in the presence of a homogeneous cobalt catalyst and an inorganic sulfur-containing additive that is capable of forming a sulfide anion ($S^{2-}$) in the reaction mixture and which suppresses the formation of cobalt carbide during the reaction.

51. The process of claim 50 wherein the inorganic sulfur-containing additive is selected from the group consisting of metal sulfides, metal hydrogen sulfides and hydrogen sulfide.

52. The process of claim 50 wherein the inorganic sulfur-containing additive is a metal sulfide having the general formula $M_xS_y$ wherein M is a metal cation and: (i) x is 1 or 2 and y is 1; or (ii) x is 2 and y is 3.

53. The process of claim 52 wherein M is a cation of a metal selected from the group consisting of sodium, potassium, calcium, magnesium and zinc.

54. The process of claim 51 wherein the inorganic sulfur-containing additive is a metal hydrogen sulfide having the general formula $M(SH)_z$ wherein M is a metal cation and z is 1, 2 or 3.

55. The process of claim 54 wherein M is a cation of a metal selected from the group consisting of sodium, potassium, calcium, magnesium and zinc.

56. The process of claim 51 wherein the inorganic sulfur-containing additive is selected from the group consisting of sodium hydrogen sulfide, sodium sulfide, and hydrogen sulfide.

57. The process of claim 56 wherein the inorganic sulfur-containing additive is hydrogen sulfide.

58. A hydroformylation process comprising reacting a compound having at least one olefinic carbon-to-carbon bond with hydrogen and carbon monoxide in the presence of a homogeneous cobalt catalyst and an organic sulfur-containing additive that is capable of forming a sulfide anion ($S^{2-}$) in the reaction mixture and which suppresses the formation of cobalt carbide during the reaction.

59. The process of claim 58 wherein the organic sulfur-containing compound has a thiol functional group.

60. The process of claim 59 wherein the organic sulfur-containing compound has the general formula $R^5$—SH, wherein $R^5$ is a lower alkyl or aryl.

61. The process of claim 58 wherein the organic sulfur-containing compound has a disulfide linkage.

62. The process of claim 61 wherein the organic sulfur-containing compound has the general formula $R^6$—SS—$R^7$, wherein $R^6$ and $R^7$ each independently represent a lower alkyl or aryl.

63. The process of claim 58 wherein the organic sulfur-containing compound has a thioether linkage.

64. The process of claim 63 wherein the organic sulfur-containing compound has the general formula $R^6$—S—$R^7$, wherein $R^6$ and $R^7$ each independently represent a lower alkyl or aryl.

65. The process of claim 64 wherein the organic sulfur-containing compound is dimethylsulfide.

66. The process of claim 58 wherein the organic sulfur-containing compound comprises a thiophene compound.

67. The process of claim 58 wherein the organic sulfur-containing compound is selected from the group consisting of thiophene and dimethyldisulfide.

68. The process of claim 1 wherein the sulfur-containing compound is present in an amount of from 50 to 80 parts per million by weight of the total reaction mixture.

69. The process of claim 50 wherein the sulfur-containing compound is present in an amount of from 50 to 80 parts per million by weight of the total reaction mixture.

70. The process of claim 58 wherein the sulfur-containing compound is present in an amount of from 50 to 80 parts per million by weight of the total reaction mixture.

* * * * *